(12) United States Patent
Ishii et al.

(10) Patent No.: US 7,462,734 B2
(45) Date of Patent: Dec. 9, 2008

(54) PROCESS FOR PRODUCTION OF OPTICALLY ACTIVE α-FLUORO-CARBOXYLIC ESTER DERIVATIVES

(75) Inventors: Akihiro Ishii, Saitama (JP); Hideyuki Tsuruta, Saitama (JP); Takashi Ootsuka, Saitama (JP); Yokusu Kuriyama, Saitama (JP); Manabu Yasumoto, Saitama (JP); Kenjin Inomiya, Saitama (JP); Koji Ueda, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 204 days.

(21) Appl. No.: 11/597,105

(22) PCT Filed: Aug. 5, 2005

(86) PCT No.: PCT/JP2005/014426

§ 371 (c)(1),
(2), (4) Date: Nov. 20, 2006

(87) PCT Pub. No.: WO2006/018991

PCT Pub. Date: Feb. 23, 2006

(65) Prior Publication Data
US 2008/0103327 A1 May 1, 2008

(30) Foreign Application Priority Data
Aug. 18, 2004 (JP) .............................. 2004-237883

(51) Int. Cl.
C07C 69/76 (2006.01)
C07C 69/63 (2006.01)
C07C 33/46 (2006.01)
C07C 31/34 (2006.01)

(52) U.S. Cl. ...................... 560/111; 560/227; 568/812; 568/842

(58) Field of Classification Search ........................ None
See application file for complete search history.

(56) References Cited

U.S. PATENT DOCUMENTS

| 5,760,255 | A | 6/1998 | Vorbruggen et al. |
| 6,080,886 | A | 6/2000 | Lal et al. |
| 6,248,889 | B1 | 6/2001 | Savu et al. |
| 2003/0225301 | A1 | 12/2003 | Amano et al. |

FOREIGN PATENT DOCUMENTS

| JP | 3-184929 A | 8/1991 |
| JP | 11-171858 A | 6/1999 |
| JP | 2003-267923 A | 9/2003 |

OTHER PUBLICATIONS

Fritz-Langhals et al., *Simple Synthesis of Optically Active 2-Fluoropropanoic Acid and Analogs of High Enantiomeric Purity*, Tetrahedron Letters, Great Britain, 1993, vol. 34, No. 2, pp. 293-296.
*Enantiomerically Pure Ethyl (R)- (S)- 2-Fluorohexanoate by Enzyme-Catalyzed Kinetic Resolution(Hexanoic acid, 2-fluoro-, ethyl ester, (R)- and (S)-)*, Organic Synthesis, US, 1990, vol. 69, pp. 10-18.
Lowe, et. al., *Synthesis Absolute Configurable, and Circular Dichroism of the Enantiomers of Fluorosuccinic Acid*, Journal of the Chemical Society, Perkin Transaction 1: Organic and Bio-Organic Chemistry (1972-1999) (UK), 1980, vol. 9, pp. 2029-2032.
Nippon Kagaku Kaisha (JP), 1983, Vo. 9, pp. 1363-1368.
Fritz-Langhals, *Alkali Metal Fluorides as Efficient Fluorinating Agents. Enantiocontrolled Synthesis of 2-Fluoroalkyl Carboxylates and 1-Fluoroalkyl Benzenes*, Tetrahedron: Asymmetry (UK), 1994, vol. 5, No. 6, pp. 981-986.
Yin et. al., *Direct and Convenient Conversion of Alcohols to Fluorides*, Organic Letters, 2004, vol. 6, No. 9, pp. 1465-1468.
Zarkowsky et. al. (Merck), *Convenient Conversion of Alcohols to Fluorides*, American Chemical Society Division of Organic Chemistry, Abstracts, 227th ACS National Meeting, 2004, 2 pp.
Focella, et. al., *Simple Stereospecific Synthesis of (R)-2-Fluorohexanoic Acid Ethyl Ester*, Synthetic Communications, 1991, vol. 21, No. 21, pp. 2165-2170.
International Search Report dated Nov. 15, 2005 with English translation of relevant portion (Five (5) pages).

*Primary Examiner*—Paul A Zucker
(74) *Attorney, Agent, or Firm*—Crowell & Moring LLP

(57) ABSTRACT

The present invention relates to a process for producing an optically active α-fluorocarboxylate derivative represented by the formula [2],

[Chemical Formula 26]

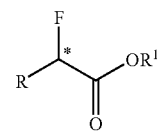

[2]

by reacting an optically active α-hydroxycarboxylate derivative with trifluoromethanesulfonyl fluoride ($CF_3SO_2F$) in the presence of an organic base, in the formula [2], R represents a straight-chain or branched-chain alkyl group of a carbon number of 1 to 12; one of or two by any combination of aromatic hydrocarbon groups, unsaturated hydrocarbon groups, straight-chain or branched alkoxy groups of a carbon number of 1 to 6, aryloxy groups, halogen atoms (fluorine, chlorine, bromine and iodine), protected carboxyl groups, protected amino groups or protected hydroxyl group can be substituted on any carbon atoms of the alkyl group; $R^1$ represents a straight-chain or branched-chain alkyl group of a carbon number of 1 to 8; any carbon atoms of the alkyl groups of R and $R^1$ may form a covalent bond; and * represents an asymmetric carbon.

9 Claims, No Drawings

US 7,462,734 B2

PROCESS FOR PRODUCTION OF OPTICALLY ACTIVE α-FLUORO-CARBOXYLIC ESTER DERIVATIVES

TECHNICAL FIELD

The present invention relates to a process for producing optically active α-fluorocarboxylate derivatives, which are important intermediates of medicines and optical materials.

BACKGROUND OF THE INVENTION

Conventional production processes of optically active α-fluorocarboxylate derivatives, which are the targets of the present invention, can roughly be separated into the following three, and their representative publications will respectively be cited.

There are disclosed 1) a process (Non-patent Publication 1) in which an optically active α-amino acid derivative is subjected to a deaminofluorination in a hydrogen fluoride/pyridine complex, 2) a process (Non-patent Publication 2) in which a racemic α-fluorocarboxylate derivative is subjected to an optical resolution through an asymmetric hydrolysis by enzyme, and 3) processes in which optically active α-hydroxycarboxylate derivatives are subjected to dehydroxyfluorination by various techniques. The production processes of 3) are related to the present invention, and there are 3-1) a process (Non-patent Publication 3) by DAST [$(C_2H_5)_2NSF_3$], 3-2) a process (Non-patent Publication 4) by a fluoroalkylamine reagent, and 3-3) a process (Non-patent Publication 5) in which the hydroxyl group is turned into a sulfonate group, followed by replacement with a fluorine anion ($F^-$).

As dehydroxyfluorination reactions using perfluoroalkanesulfonyl fluoride, there are disclosed 4) a process (Patent Publication 1 and Patent Publication 2) in which a substrate having a hydroxyl group is subjected to a dehydroxyfluorination by a perfluoroalkanesulfonyl fluoride ($RfSO_2F$; Rf represents a perfluoroalkyl group), such as perfluorobutanesulfonyl fluoride ($C_4F_9SO_2F$), in the presence of a special organic base, such as DBU (1,8-diazabicyclo[5.4.0]undec-7-ene), and 5) a process (Non-patent Publication 6 and Non-patent Publication 7) in which a substrate having a hydroxyl group is subjected to a dehydroxyfluorination by perfluorobutanesulfonyl fluoride in the presence of an organic base, such as triethylamine [$(C_2H_5)_3N$], and a fluorination agent, such as triethylamine tris(hydrogen fluoride) complex [$(C_2H_5)_3N\cdot 3HF$].

Patent Publication 1: U.S. Pat. No. 5,760,255
Patent Publication 2: U.S. Pat. No. 6,248,889
Non-patent Publication 1: Tetrahedron Letters (GB), 1993, Vol. 34, No. 2, p. 293-296
Non-patent Publication 2: Organic Syntheses (US), 1990, Vol. 69, p. 10-18
Non-patent Publication 3: Journal of the Chemical Society, Perkin
Transactions 1: Organic and Bio-Organic Chemistry (1972-1999) (UK), 1980, Vol. 9, p. 2029-2032
Non-patent Publication 4: Nippon Kagaku Kaishi (JP), 1983, Vol. 9, p. 1363-1368
Non-patent Publication 5: Tetrahedron; Asymmetry (UK), 1994, Vol. 5, No. 6, p. 981-986
Non-patent Publication 6: Organic Letters (US), 2004, Vol. 6, No. 9, p. 1465-1468
Non-patent Publication 7: 227th ACS Spring National Meeting Abstracts, Mar. 28 to Apr. 1, 2004, ORGN 198, D. Zarkowsky et al. (Merck)

SUMMARY OF THE INVENTION

It is an object of the present invention to provide an industrial production process of optically active α-fluorocarboxylate derivatives, which are important intermediates of medicines and optical materials.

It has not been possible to obtain α-fluorocarboxylate derivatives with high optical purity by the production processes of Non-patent Publication 1 and Non-patent Publication 2. In the production process of Non-patent Publication 2, yield has never exceeded 50% since it is optical resolution of a racemate. In the production process of Non-patent Publication 3, it has been necessary to use DAST, which has a very high price and is dangerous when used in a large amount. In the production process of Non-patent Publication 5, it has been necessary to separately conduct the step of turning the hydroxyl group into a sulfonate group and the step of replacing with a fluorine anion ($F^-$). Furthermore, there have been problems in which the optical purity reduction is significantly recognized during the two steps, and in which optical purity of the optically active α-hydroxycarboxylate derivative used as the substrate is not reflected in optical purity of an optically active α-fluorocarboxylate derivative, which is the target product.

In Patent Publication 1, Patent Publication 2, Non-patent Publication 6 and Non-patent Publication 7, dehydroxyfluorination reactions of a substrate having a hydroxyl group using a perfluoroalkanesulfonyl fluoride are broadly disclosed, and they have a merit of being able to continuously conduct in a single reactor the step of turning the hydroxyl group into a sulfonate group (a perfluoroalkanesulfonate group) and the step of replacing it with a fluorine anion ($F^-$). However, they use a perfluoroalkanesulfonyl fluoride of a carbon number of 4 or greater, of which long-term persistence in environment and toxicity are pointed out, and of which industrial use is limited [for example, see FARUMASHIA Vol. 40, No. 2, 2004 with respect to long-term persistence and toxicity of perfluorooctanesulfonic acid derivatives]. Furthermore, in the production processes of Patent Publication 1 and Patent Publication 2, it has been necessary to use a special organic base, such as high-price DBU, in industrial uses. In the production processes of Non-patent Publication 6 and Non-patent Publication 7, it has been necessary to add a fluorination agent, such as triethylamine tris(hydrogen fluoride) complex, in addition to perfluorobutanesulfonyl fluoride.

In dehydroxyfluorination reactions of Patent Publication 1, Patent Publication 2, Non-patent Publication 6 and Non-patent Publication 7, perfluoroalkanesulfonyl fluoride subjects a hydroxyl group of the substrate to perfluoroalkanesulfonylation, and it is released as a perfluoroalkanesulfonate anion ($RfSO_3^-$; Rf represents a perfluoroalkyl group) in the subsequent replacement reaction with fluorine anion ($F^-$). Therefore, mentioning from the viewpoint of atom economy of fluorine, one with a shorter carbon chain is more advantageous in industrial uses [perfluorooctanesulfonyl fluoride ($C_8F_{17}SO_2F$)<perfluorobutanesulfonyl fluoride<trifluoromethanesulfonyl fluoride ($CF_3SO_2F$)], as long as it has a sufficient sulfonylation capability and a sufficient releasing capability. A dehydroxyfluorination reaction using trifluoromethanesulfonyl fluoride has not specifically been disclosed therein. Furthermore, in the dehydroxyfluorination reaction of Non-patent Publication 7 having a system of trifluoromethanesulfonic anhydride, triethylamine tris(hydrogen fluoride) complex and triethylamine, it is disclosed therein that gaseous trifluoromethanesulfonyl fluoride (boiling point: −21° C.) is formed in the reaction system, thereby not achieving an efficient trifluoromethanesulfonylation of a hydroxyl group of the substrate, and that a combination with high-boiling-point (64° C.) perfluorobutanesulfonyl fluoride (a system of perfluorobutanesulfonyl fluoride, triethylamine tris(hydrogen fluoride) complex and triethylamine) is preferable. It has clearly been described therein that low-boiling-point trifluoromethanesulfonyl fluoride is not preferable as a perfluoroalkanesulfonyl fluoride of the dehydroxyfluorination agent.

Furthermore, as a preferable substrate of the dehydroxyfluorination reactions of Patent Publication 1, Patent Publication 2, Non-patent Publication 6 and Non-patent Publication 7, an optically active α-hydroxycarboxylate derivative, which is the target of the present invention, is not disclosed. It has not been disclosed that the dehydroxyfluorination reaction can be applied to a production process of optically active α-fluorocarboxylate derivatives of high optical purity.

Thus, there has been a strong demand for a process capable of industrially producing optically active α-fluorocarboxylate derivatives.

The present inventors have conducted an eager examination for solving the above-mentioned task. As a result, we have made it clear that optically active α-fluorocarboxylate derivatives can be produced by reacting optically active α-hydroxycarboxylate derivatives with trifluoromethanesulfonyl fluoride in the presence of an organic base, such as triethylamine, which is industrially low in price and generally used.

The characteristic of the present production process resides in that trifluoromethanesulfonylation of an optically active α-hydroxycarboxylate derivative proceeds well by using trifluoromethanesulfonyl fluoride, and the subsequent fluorine substitution reaction proceeds well by only a hydrogen fluoride salt or complex of an organic salt, such as triethylamine, that has been produced in the same amount in the reaction system in the trifluoromethanesulfonylation. The substrate that makes the dehydroxyfluorination reaction proceed well under such a reaction condition has not been disclosed yet in prior art publications. It is due to the substrate specificity of optically active α-hydroxycarboxylate derivatives. We have made it clear that the reduction of the optical purity is almost not found under reaction conditions of the dehydroxyfluorination, and optical purity of the optically active α-hydroxycarboxylate derivative used as the substrate is reflected in optical purity of an optically active α-fluorocarboxylate derivative, which is the target product.

According to the present invention, there is provided a process for producing an optically active α-fluorocarboxylate derivative represented by the formula [2],

[Chemical Formula 2]

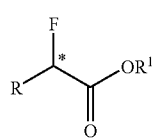

[2]

by reacting an optically active α-hydroxycarboxylate derivative represented by the formula [1],

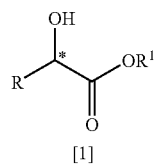

[Chemical Formula 1]

[1]

with trifluoromethanesulfonyl fluoride ($CF_3SO_2F$) in the presence of an organic base, in the formulas [1] and [2], R represents a straight-chain or branched-chain alkyl group of a carbon number of 1 to 12; one of or two by any combination of aromatic hydrocarbon groups, unsaturated hydrocarbon groups, straight-chain or branched alkoxy groups of a carbon number of 1 to 6, aryloxy groups, halogen atoms (fluorine, chlorine, bromine and iodine), protected carboxyl groups, protected amino groups or protected hydroxyl group can be substituted on any carbon atoms of the alkyl group; $R^1$ represents a straight-chain or branched-chain alkyl group of a carbon number of 1 to 8; any carbon atoms of the alkyl groups of R and $R^1$ may form a covalent bond; and * represents an asymmetric carbon.

DETAILED DESCRIPTION

The production process of the present invention is a means that can be conducted industrially with the lowest price among the production processes of optically active α-fluorocarboxylate derivatives, which have been disclosed up to now in prior art publications. Advantageous points of the production process of the present invention compared with prior art will be described in the following.

Relative to Non-patent Publication 1 and Non-patent Publication 2, it is possible to obtain the target product of high optical purity by using a substrate of high optical purity, since optical purity of the optically active α-hydroxycarboxylate derivative used as the substrate is reflected in optical purity of an optically active α-fluorocarboxylate derivative, which is the target product.

Relative to Non-patent Publication 2, yield is not limited to 50%, since it is a conversion of an optically active α-hydroxycarboxylate derivative to an optically active α-fluorocarboxylate derivative by a dehydroxyfluorination reaction.

Relative to Non-patent Publication 3, it is not necessary to use a reagent, such as DAST, that is very expensive and dangerous when used in large amounts.

Relative to Non-patent Publication 5, it is possible to continuously conduct in a single reactor the step of turning the hydroxyl group into a sulfonate group and the step of replacing with a fluorine anion ($F^-$). Under the reaction condition of the dehydroxyfluorination, the reduction of optical purity is almost not found. Optical purity of the optically active α-hydroxycarboxylate derivative used as the substrate is reflected in optical purity of an optically active α-fluorocarboxylate derivative, which is the target product.

Relative to Patent Publication 1, Patent Publication 2, Non-patent Publication 6 and Non-patent Publication 7, it is not necessary to use a long-carbon-chain perfluoroalkanesulfonyl fluoride that is problematic in long-term persistence in environment and toxicity, and it is possible to use trifluoromethanesulfonyl fluoride, which is highest in atomic economy of fluorine. Relative to Patent Publication 1 and Patent Publication 2, it is not necessary to use an expensive special organic base, such as DBU, in industrial uses. Relative to Non-patent Publication 6 and Non-patent Publication 7, it is not necessary to separately add a fluorination agent, such as triethylamine tris(hydrogen fluoride) complex. In the production process of the present invention, the fluorine substitution reaction proceeds well by only a hydrogen fluoride salt or complex of an organic base, such as triethylamine, produced as a by-product in the same amount in the reaction system in trifluoromethanesulfonylation.

In the dehydroxyfluorination reaction of an optically active α-hydroxycarboxylate derivative by perfluoroalkanesulfonyl fluoride, which is the target of the present invention, it is not possible to obtain the target product, an optically active α-fluorocarboxylate derivative, with good yield by using DBU, which is disclosed as a preferable organic base in Patent Publication 1 and Patent Publication 2, and a new advantageous effect of the present invention that the use of triethylamine disclosed in the present invention is preferable was found (Example 3 vs. Comparative Example 1 and Comparative Example 2). DBU is classified into organic bases that are stronger in basicity than that of triethylamine. It is considered that this strong basicity causes hydrolysis of a carboxylate group and side reactions such as that a perfluoroalkanesulfonic acid is released from a perfluoroalkanesulfonic acid ester to produce unsaturated compounds as by-products. Therefore, in the dehydroxyfluorination reaction of an optically active α-hydroxycarboxylate derivative by perfluoroalkanesulfonyl fluoride, which is the target of the present invention, the use of an organic base, such as triethylamine, that is weaker than DBU is preferable. A preferable combination with the organic base depends largely on the substrate specificity of the optically active α-hydroxycarboxylate derivative.

The dehydroxyfluorination reaction having characteristics disclosed in the present invention is not disclosed in Patent Publication 1, Patent Publication 2, Non-patent Publication 6 and Non-patent Publication 7 of dehydroxyfluorination reactions using conventional perfluoroalkanesulfonyl fluorides. There is no disclosure either that it can preferably be applied to the production process of optically active α-fluorocarboxylate derivatives, which are the targets of the present invention.

The production process of the present invention is an extremely useful process for industrially producing optically active α-fluorocarboxylate derivatives, since it is high in selectivity and does almost not produce impurities that are difficult in separation.

In the following, the production process of optically active α-fluorocarboxylate derivatives of the present invention will be explained in detail.

The present production process comprises reacting an optically active α-hydroxycarboxylate derivative represented by the formula [1] with trifluoromethanesulfonyl fluoride in the presence of an organic base. Furthermore, the obtained optically active α-fluorocarboxylate derivative may be reacted with a hydride reducing agent (scheme 1).

[Chemical Formula 3]

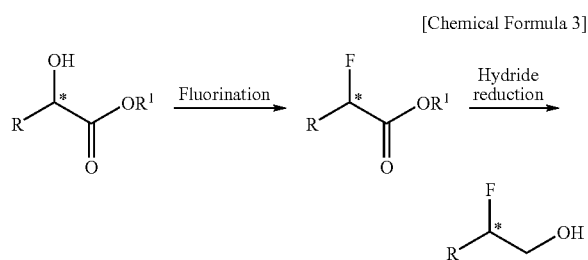

Firstly, in the fluorination of the first step, trifluoromethanesulfonylation of an optically active α-hydroxycarboxylate derivative represented by the formula [1] proceeds, and then the fluorine substitution reaction proceeds by a hydrogen fluoride salt or complex of an organic base produced as a by-product in the reaction system, thereby giving the target product, an optically active x-fluorocarboxylate derivative represented by the formula [2]. In the present fluorination, it is an important characteristic that the subsequent fluorine substitution reaction proceeds well by only a hydrogen fluoride or complex of an organic base, such as triethylamine, produced as a by-product in the same amount in the reaction system in the trifluoromethanesulfonylation. Therefore, it is preferable to conduct the fluorination without using a fluorination agent (triethylamine tris(hydrogen fluoride) complex or the like) besides trifluoromethanesulfonyl fluoride. In the trifluoromethanesulfonylation, stereochemistry of α-position is maintained, and the stereochemistry of α-position is reversed in the subsequent fluorine substitution reaction. Therefore, an α-position S configuration of optically active α-fluorocarboxylate derivative is obtained from α-position R configuration of optically active α-hydroxycarboxylate derivative, and similarly α-position R configuration is obtained from α-position S-configuration.

As R of optically active α-hydroxycarboxylate derivative represented by the formula [1], there are cited methyl group, ethyl group, propyl group, butyl group, amyl group, hexyl group, heptyl group, octyl group, nonyl group, decyl group, undecyl group, and lauryl group. The alkyl groups having a carbon number of not less than three can have a straight chain or branch. One of or two by any combination of aromatic hydrocarbon groups, such as phenyl group and naphthyl group, unsaturated hydrocarbon groups, such as vinyl group, straight-chain or branched alkoxy groups of a carbon number of 1 to 6, aryloxy groups, such as phenoxy group, halogen atoms (fluorine, chlorine, bromine and iodine), protected carboxyl groups, protected amino groups or protected hydroxyl group can be substituted on any carbon atoms of the alkyl group. As protecting groups of carboxyl group, amino group and hydroxyl group, it is possible to use protecting groups described in Protective Groups in Organic Synthesis, Third Edition, 1999, John Wiley & Sons, Inc. Specifically, ester group and the like are cited as protecting groups of carboxylic group; benzyl group, acyl group (acetyl group, chloroacetyl group, benzoyl group, 4-methylbenzoyl group and the like), phthaloyl group and the like are cited as protecting groups of amino group; benzyl group, 2-tetrahydropyranyl group, acyl group (acetyl group, chloroacetyl group, benzoyl group, 4-methylbenzoyl group and the like), silyl group (trialkylsilyl group, alkylarylsilyl group and the like) and the like are cited as protecting groups of hydroxyl group. In particular, a protecting group to form 2,2-dimethyl-1,3-dioxolane and the like are cited as protecting groups of 1,2-dihydroxyl group.

It is possible to use the production process, which is the target of the present invention, even in case that R of optically active α-hydroxycarboxylate derivative represented by the formula [1] is an aromatic hydrocarbon group, which refers to one that the aromatic ring is directly bonded to the optically active carbon (C*) of the compound, such as phenyl group and tolyl group. In this case, however, optical purity of the target product, the optically active α-fluorocarboxylate derivative represented by the formula [2], lowers significantly, as compared with the case that R is an alkyl group or the above-mentioned substituted alkyl group. With this, an alkyl group or the above-mentioned substituted alkyl group is preferable as R of the optically active α-hydroxycarboxylate derivative represented by the formula [1] (there is also disclosed in Non-patent Publication 5 a similar phenomenon that the fluorinated compound as the target product is obtained as a racemic mixture in the case of using an optically active mandelate derivative as the substrate).

Optical purity reduces significantly in the case of directly bonding an aromatic hydrocarbon group to the asymmetric carbon (C*). However, such optical purity reduction does not occur in case that an aromatic hydrocarbon group exists as a substituent through one or more atoms of alkyl carbon (i.e., a substituted alkyl group) (for example, Ph-CH$_2$CH$_2$ group shown in Example 3).

As R$^1$ of optically active α-hydroxycarboxylate derivative represented by the formula [1], there are cited methyl group, ethyl group, propyl group, butyl group, amyl group, hexyl group, heptyl group, and octyl group. The alkyl groups having a carbon number of not less than three can have a straight chain or branch. Any carbon atoms of the alkyl groups of R and R$^1$ of optically active α-hydroxycarboxylate derivative represented by the formula [1] can form a covalent bond to take a lactone.

Stereochemistry of asymmetric carbon of optically active α-hydroxycarboxylate derivative represented by the formula [1] can take R configuration or S configuration. Enantiomeric excess (% ee) is not particularly limited. It suffices to use one with 90% ee or greater. Normally, 95% ee or greater is preferable, and particularly 97% ee or greater is more preferable.

Referring to Synthetic Communications (US), 1991, Vol. 21, No. 21, p. 2165-2170, it is possible to similarly produce optically active α-hydroxycarboxylate derivatives represented by the formula [1] from various optically active α-amino acids on the market. Commercial products were used as (S)-ethyl lactate and (R)-4-phenyl-2-hydroxy ethyl butanoate, which were used in Examples and Comparative Examples.

The amount of trifluoromethanesulfonyl fluoride for use is not particularly limited. It suffices to use 1 mol or greater relative to 1 mol of optically active α-hydroxycarboxylate derivative represented by the formula [1]. Normally, 1 to 10 mols is preferable, and particularly 1 to 5 mols is more preferable. As mentioned above, it is an important characteristic in the present invention that the subsequent fluorine substitution reaction proceeds well by only a hydrogen fluoride salt or complex of an organic base, such as triethylamine, that is produced as a by-product in the same amount in the reaction system in the trifluoromethanesulfonylation. To make an advantage of conducting without using a fluorination agent besides trifluoromethanesulfonyl fluoride, it is more preferable that the amount of trifluoromethanesulfonyl fluoride for use is from equimolar to 1 to 3 mols of slight excess relative to 1 mol of optically active α-hydroxycarboxylate derivative.

As the organic base, there are cited trimethylamine, triethylamine, diisopropylethylamine, tri-n-propylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, and the like. Of these, triethylamine, duisopropylethylamine, tri-n-propylamine, pyridine, 2,3-lutidine, 2,4-lutidine, 2,6-lutidine, 3,4-lutidine, 3,5-lutidine, 2,4,6-collidine, and 3,5,6-collidine are preferable. In particular, triethylamine, diusopropylethylamine, pyridine, 2,4-lutidine, 2,6-lutidine, 3,5-lutidine, and 2,4,6-collidine are more preferable.

The amount of the organic base for use is not particularly limited. It suffices to use 1 mol or greater relative to 1 mol of optically active α-hydroxycarboxylate derivative represented by the formula [1]. Normally, 1 to 10 mols is preferable, and particularly 1 to 5 mols is more preferable.

As the reaction solvent, there are cited aliphatic hydrocarbon series such as n-hexane, cyclohexane, and n-heptane; aromatic hydrocarbon series such as benzene, toluene, xylene, and mesitylene; halogenated hydrocarbon series such as methylene chloride, chloroform, and 1,2-dichloroethane; ether series such as diethyl ether, tetrahydrofuran, and tert-butyl methyl ether; ester series such as ethyl acetate and n-butyl acetate; amide series such as N,N-dimethylformamide, N,N-dimethylacetamide, and 1,3-dimethyl-2-imidazolidinone; nitrile series such as acetonitrile and propionitrile; dimethylsulfoxide; and the like. Of these, n-heptane, toluene, xylene, mesitylene, methylene chloride, tetrahydrofuran, ethyl acetate, N,N-dimethylformamide, acetonitrile, and dimethylsulfoxide are preferable. In particular, toluene, mesitylene, methylene chloride, tetrahydrofuran, ethyl acetate, N,N-dimethylformamide, and acetonitrile are more preferable. These reaction solvents can be used singly or in combination.

The amount of the reaction solvent for use is not particularly limited. It suffices to use 0.1 L (liter) or greater to 1 mol of optically active α-hydroxycarboxylate derivative represented by the formula [1]. Normally, 0.1-20 L is preferable. Particularly, 0.1-10 L is more preferable.

The temperature condition is −100 to +100° C. Normally, −80 to +80° C. is preferable. Particularly, −60 to +60° C. is more preferable. It is possible to use a pressure-proof reaction vessel in case that the reaction is conducted under a temperature condition of boiling point or higher of trifluoromethanesulfonyl fluoride.

Although the reaction time is 0.1 to 48 hours, it varies depending on the substrate and the reaction conditions. Therefore, it is preferable to determine the time, at which the raw material has almost disappeared, as the end point, while tracing the progress of the reaction by an analytical means such as gas chromatography, liquid chromatography, or NMR.

The post treatment is not particularly limited. Normally, it is possible to obtain a crude product by pouring the reaction-terminated liquid into an aqueous solution of an inorganic base of alkali metal (e.g., sodium hydrogencarbonate, potassium hydrogencarbonate, sodium carbonate or potassium carbonate, or the like), washing the recovered organic layer with water and with an aqueous solution of inorganic acid (e.g., hydrogen chloride, hydrogen bromide, nitric acid or sulfuric acid or the like) or an aqueous solution of calcium chloride, and directly conducting a fractional distillation. It is possible to obtain the target product, optically active α-fluorocarboxylate derivative represented by the formula [2], with high chemical purity by conducting a rectification according to need.

Next, in the hydride reduction of the second step, optically active α-fluorocarboxylate derivative represented by the formula [2] obtained by the fluorination of the first step is reacted with a hydride reducing agent, thereby giving optically active 2-fluoroalcohol derivative represented by the formula [7]. In the present hydride reduction, stereochemistry of a carbon atom, on which a fluorine atom has been substituted, is maintained. Thus, the second-position R configuration of the optically active 2-fluoroalcohol derivative is obtained from α-position R configuration of the optically active α-fluorocarboxylate derivative, and similarly the second-position S configuration is obtained from the α-position S configuration. The present hydride reduction can be conducted similarly by referring to known methods such as Japanese Patent No. 2879456 specification.

As the hydride reducing agent, there are cited aluminum hydride series such as (i-Bu)$_2$AlH, LiAlH$_4$, and NaAlH$_2$(OCH$_2$CH$_2$OCH$_3$)$_2$; boron hydride series such as diborane, BH$_3$.tetrahydrofuran, BH$_3$.S(CH$_3$)$_2$, BH$_3$.N(CH$_3$)$_3$, NaBH$_4$, and LiBH$_4$ (i-Bu represents an isobutyl group). Of these, (i-Bu)$_2$AlH, LiBH$_4$, NaAlH$_2$(OCH$_2$CH$_2$OCH$_3$)$_2$, diborane, BH$_3$.tetrahydrofuran, NaBH$_4$, and LiBH$_4$ are preferable. In particular, (i-Bu)$_2$AlH, LiAlH$_4$, and NaAlH$_2$(OCH$_2$CH$_2$OCH$_3$)$_2$ are more preferable. These hydride reducing agents can also be used in the presence of various inorganic salts.

The amount of the hydride reducing agent for use is not particularly limited. It suffices to use 0.5 mols or greater to 1 mol of optically active α-fluorocarboxylate derivative represented by the formula [2]. Normally, 0.5-5 mols is preferable. In particular, 0.5-3 mols is preferable.

As the reaction solvent, there are cited aliphatic hydrocarbon series such as n-hexane, cyclohexane, and n-heptane; aromatic hydrocarbon series such as benzene, toluene, xylene, and mesitylene; halogenated hydrocarbon series such as methylene chloride, chloroform, and 1,2-dichloroethane; ether series such as diethyl ether, tetrahydrofuran, tert-butyl methyl ether, and 1,4-dioxane; alcohol series such as methanol, ethanol, n-propanol, and i-propanol; and the like. Of these, n-heptane, toluene, mesitylene, methylene chloride, diethyl ether, tetrahydrofuran, tert-butyl methyl ether, 1,4-dioxane, methanol, ethanol, and i-propanol are preferable. In particular, toluene, mesitylene, tetrahydrofuran, tert-butyl methyl ether, methanol, and ethanol are more preferable. These reaction solvents can be used singly or in combination.

The amount of the reaction solvent for use is not particularly limited. It suffices to use 0.1 L (liter) or greater to 1 mol of optically active α-fluorocarboxylate derivative represented by the formula [2]. Normally, 0.1 to 20 L is preferable. Particularly, 0.1-10 L is more preferable.

The temperature condition is −100 to +100° C. Normally, −80 to +80° C. is preferable. Particularly, −60 to +60° C. is more preferable.

Although the reaction time is 0.1 to 24 hours, it varies depending on the substrate and the reaction conditions. Therefore, it is preferable to determine the time, at which the raw material has almost disappeared, as the end point, while tracing the progress of the reaction by an analytical means such as gas chromatography, liquid chromatography, or NMR.

The post treatment is not particularly limited. Normally, water, sodium sulfate hydrate, methanol or ethanol, or the like is added to the reaction-terminated liquid to decompose the hydride reducing agent used excessively, followed by filtering inorganic matters and conducting fractional distillation of the filtrate. With this, it is possible to obtain a crude product. It is possible to obtain the target product, optically active 2-fluoroalcohol derivative represented by the formula [7], with high chemical purity by conducting rectification according to need.

EXAMPLES

In the following, embodiments of the present invention are specifically explained by examples and comparative examples, but the present invention is not limited to these examples.

Example 1

A pressure-proof reaction vessel made of stainless steel (SUS) was charged with 137.00 g (1159.74 mmol, 1.00 eq, optical purity: 98.5% ee) of an optically active α-hydroxycarboxylate derivative represented by the following formula,

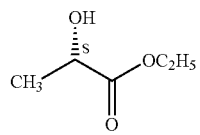

[Chemical Formula 4]

380 ml of mesitylene, and 120.10 g (1186.88 mmol, 1.02 eq) of triethylamine, followed by lowering the inside temperature to around −40° C. and bubbling 208.80 g (1373.05 mmol, 1.18 eq) of trifluoromethanesulfonyl fluoride from a cylinder. With stirring, it was returned to room temperature by spending about 4 hours, and furthermore stirring was conducted at room temperature for about 15 hours. Conversion of the reaction was found by gas chromatography measurement to be 99.8%. The reaction-terminated liquid separated into two layers was poured into 1,200 ml of 10% potassium carbonate aqueous solution to wash the organic layer. The recovered organic layer was washed with 1,400 ml of 1N hydrogen chloride aqueous solution and then 400 ml of 10% calcium chloride aqueous solution, followed by drying with 50 g of anhydrous sodium sulfate and filtering, thereby obtaining 410.40 g of a mesitylene solution of a crude product of optically active α-fluorocarboxylate derivative represented by the following formula.

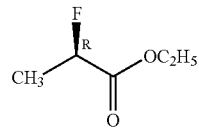

[Chemical Formula 5]

The total amount of the mesitylene solution of the obtained crude product was subjected to fractional distillation, thereby recovering 99.63 g (boiling point: 120-127° C./normal pressure) as a main distillate. It was found by $^1$H-NMR spectrum of the main distillate that 3.7% of mesitylene were contained. The total yield was 69% (the total yield by combining the latter distillate and the residue: 72%). Gas chromatography purity of the main distillate was 100.0% (except mesitylene). $^1$H-NMR spectrum and $^{19}$F-NMR spectrum of the optically active α-fluorocarboxylate derivative are shown in the following.

$^1$H-NMR (standard substance: $(CH_3)_4Si$, heavy solvent: $CDCl_3$), δppm: 1.32 (t, 7.2 Hz, 3H), 1.58 (dd, 23.6 Hz, 6.9 Hz, 3H), 4.26 (q, 7.2 Hz, 2H), 5.00 (dq, 49.0 Hz, 6.9 Hz, 1H).

19F-NMR (standard substance: $C_6F_6$, heavy solvent: $CDCl_3$), δppm: −21.88 (dq, 48.9 Hz, 24.4 Hz, 1 F).

Example 2

A tetrahydrofuran solution (the amount of tetrahydrofuran used: 160 ml) containing 97.97 g (chemical purity: 96.3%, 785.42 mmol, 1.00 eq) of an optically active α-fluorocarboxylate derivative represented by the following formula,

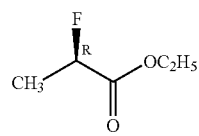

[Chemical Formula 6]

was gradually added to a tetrahydrofuran solution (the amount of tetrahydrofuran used: 630 ml) containing 22.70 g (598.00 mmol, 0.76 eq) of aluminum lithium hydride under cooling with ice, while controlling the inside temperature to 10° C. or lower, followed by stirring at the same temperature for 20 minutes and furthermore stirring at room temperature for 2 hours and 10 minutes. Conversion of the reaction was found by gas chromatography measurement to be 100%. Sodium sulfate decahydrate was gradually added to the reaction-terminated liquid under cooling with ice, while controlling the inside temperature to 12° C. or lower to mostly decompose aluminum lithium hydride used excessively. Furthermore, stirring was conducted for about 1 hour, while adding sodium sulfate decahydrate at 50-60° C. In total, 149.40 g (463.63 mmol, 0.59 eq) of sodium sulfate decahydrate were added. After the temperature was lowered to room temperature, 65.00 g (457.62 mmol, 0.58 eq) of anhydrous sodium sulfate were added for drying, followed by filtrating inorganic matters and washing the inorganic matters with 80 ml of tetrahydrofuran two times, thereby obtaining a tetrahydrofuran solution of a crude product of optically active 2-fluoroalcohol derivative represented by the following formula.

[Chemical Formula 7]

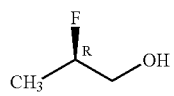

The total amount of the tetrahydrofuran solution of the obtained crude product was subjected to fractional distillation, thereby recovering 36.77 g (boiling point: 108 to 110° C./normal pressure) as a main distillate. It was found by $^1$H-NMR spectrum of the main distillate that 5.0% of mesitylene were contained. The total yield was 57% (the total yield by combining the initial distillate and the residue: 75%). Gas chromatography purity of the main distillate was 99.8% (except mesitylene). Optical purity of the main distillate was determined by converting it to a Mosher's acid ester, followed by gas chromatography. With this, it was 98.0% ee (R configuration). $^1$H-NMR spectrum and $^{19}$F-NMR spectrum of the optically active 2-fluoroalcohol derivative are shown in the following.

$^1$H-NMR (standard substance: $(CH_3)_4Si$, heavy solvent: $CDCl_3$), δppm: 1.33 (dd, 23.6 Hz, 6.4 Hz, 3H), 2.00 (br, 1H), 3.50-3.85 (m×2, 2H), 4.76 (dm, 49.6 Hz, 1H).

$^{19}$F-NMR (standard substance: $C_6F_6$, heavy solvent: $CDCl_3$), δppm: −21.40 (d/sextet, 48.9 Hz, 24.4 Hz, 1 F).

Example 3

A pressure-proof reaction vessel made of stainless steel (SUS) was charged with 2.00 g (9.60 mmol, 1.00 eq, optical purity: 99.2% ee) of an optically active α-hydroxycarboxylate derivative represented by the following formula,

[Chemical Formula 8]

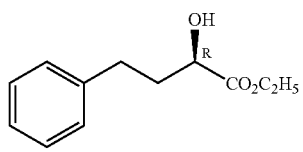

10 ml of toluene and 2.00 g (19.76 mmol, 2.06 eq) of triethylamine, followed by immersing the reaction vessel into a dry ice/acetone bath of −78° C., bubbling 3.00 g (19.73 mmol, 2.06 eq) of trifluoromethanesulfonyl fluoride from a cylinder, immediately transferring into an iced bath, and stirring for 1 hour. Conversion of the reaction was found by gas chromatography measurement to be 100%. The reaction-terminated liquid was poured into a saturated sodium hydrogencarbonate aqueous solution, followed by extraction with toluene. The recovered organic layer was dried with anhydrous sodium sulfate, followed by filtration, thereby obtaining 2.18 g of a crude product of an optically active α-fluorocarboxylate derivative represented by the following formula.

[Chemical Formula 9]

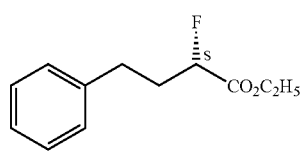

The content was calculated by internal standard method (internal standard substance: $C_6F_6$) by $^{19}$F-NMR spectrum of the crude product. With this, 1.52 g of the optically active α-fluorocarboxylate derivative represented by the above formula were contained, and yield was 75%. Optical purity of the obtained optically active α-fluorocarboxylate derivative was determined by chiral liquid chromatography. It was 99.2% ee (S configuration). $^1$H-NMR spectrum and $^{19}$F-NMR spectrum of the optically active α-fluorocarboxylate derivative are shown in the following.

$^1$H-NMR (standard substance: $(CH_3)_4Si$, heavy solvent: $CDCl_3$), δppm: 1.30 (t, 7.2 Hz, 3H), 2.10-2.30 (m×2, 2H), 2.70-2.85 (m×2, 2H), 4.23 (q, 7.2 Hz, 2H), 4.88 (dt, 48.8 Hz, 6.2 Hz, 1H), 7.20-7.40 (Ar—H, 5H).

$^{19}$F-NMR (standard substance: $C_6F_6$, heavy solvent: $CDCl_3$), δppm: −31.38 (dt, 48.9 Hz, 27.4 Hz, 1 F).

Comparative Example 1

A pressure-proof reaction vessel made of stainless steel (SUS) was charged with 1.00 g (4.80 mmol, 1.00 eq, optical purity: 99.2% ee) of an optically active α-hydroxycarboxylate derivative represented by the following formula,

[Chemical Formula 10]

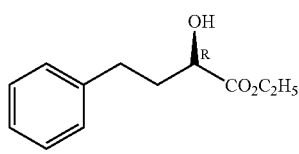

20 ml of toluene and 2.20 g (14.45 mmol, 3.01 eq) of DBU, followed by immersing the reaction vessel into a dry ice/acetone bath of −78° C., bubbling 1.10 g (7.23 mmol, 1.51 eq) of trifluoromethanesulfonyl fluoride from a bomb, immediately transferring into an iced bath, and stirring for 1 hour. Conversion of the reaction was found by gas chromatography measurement to be 100%. The reaction-terminated liquid was poured into a saturated sodium hydrogencarbonate aqueous solution, followed by extraction with toluene. The recovered organic layer was dried with anhydrous sodium sulfate, followed by filtration, thereby obtaining 0.86 g of a crude product of an optically active α-fluorocarboxylate derivative represented by the following formula.

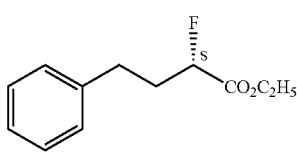

The content was calculated by internal standard method (internal standard substance: $C_6F_6$) by $^{19}$F-NMR spectrum of the crude product. With this, 0.32 g of the optically active α-fluorocarboxylate derivative represented by the above formula were contained, and yield was 32%. Optical purity of the obtained optically active α-fluorocarboxylate derivative was determined by chiral liquid chromatography. It was 99.2% ee (S configuration). $^1$H-NMR spectrum and $^{19}$F-NMR spectrum of the optically active α-fluorocarboxylate derivative were similar to those obtained in Example 3.

Comparative Example 2

A glass reaction vessel was charged with 1.00 g (4.80 mmol, 1.00 eq, optical purity: 99.2% ee) of an optically active α-hydroxycarboxylate derivative represented by the following formula,

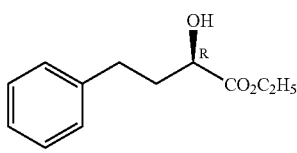

20 ml of toluene and 2.20 g (14.45 mmol, 3.01 eq) of DBU, followed by immersing the reaction vessel into an iced bath of 0° C., adding 2.15 g (7.12 mmol, 1.48 eq) of perfluorobutanesulfonyl fluoride, and stirring at the same temperature for 1 hour. Conversion of the reaction was found by gas chromatography measurement to be 100%. The reaction-terminated liquid was poured into a saturated sodium hydrogencarbonate aqueous solution, followed by extraction with toluene. The recovered organic layer was dried with anhydrous sodium sulfate, followed by filtration, thereby obtaining 1.17 g of a crude product of an optically active α-fluorocarboxylate derivative represented by the following formula.

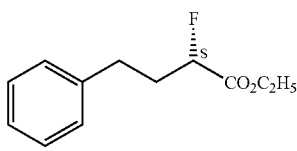

The content was calculated by internal standard method (internal standard substance: $C_6F_6$) by $^{19}$F-NMR spectrum of the crude product. With this, 0.42 g of the optically active α-fluorocarboxylate derivative represented by the above formula were contained, and yield was 42%. Optical purity of the obtained optically active α-fluorocarboxylate derivative was determined by chiral liquid chromatography. It was 98.7% ee (S configuration). $^1$H-NMR spectrum and $^{19}$F-NMR spectrum of the optically active α-fluorocarboxylate derivative were similar to those obtained in Example 3.

The invention claimed is:

1. A process for producing an optically active α-fluorocarboxylate derivative represented by the formula [2],

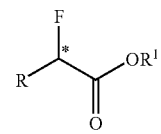

by reacting an optically active α-hydroxycarboxylate derivative represented by the formula [1],

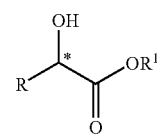

with trifluoromethanesulfonyl fluoride ($CF_3SO_2F$) in the presence of an organic base,
in the formulas [1] and [2], R represents a straight-chain or branched-chain alkyl group of a carbon number of 1 to 12; one of or two by any combination of aromatic hydrocarbon groups, unsaturated hydrocarbon groups, straight-chain or branched alkoxy groups of a carbon number of 1 to 6, aryloxy groups, halogen atoms (fluorine, chlorine, bromine and iodine), protected carboxyl groups, protected amino groups or protected hydroxyl group can be substituted on any carbon atoms of the alkyl group; $R^1$ represents a straight-chain or branched-chain alkyl group of a carbon number of 1 to 8; any carbon atoms of the alkyl groups of R and $R^1$ may form a covalent bond; and * represents an asymmetric carbon.

2. A process for producing an optically active α-fluorocarboxylate derivative represented by the formula [4],

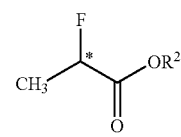

wherein $R^2$ represents a methyl group, ethyl group or isopropyl group, and * represents an asymmetric carbon, by reacting an optically active α-hydroxycarboxylate derivative represented by the formula [3],

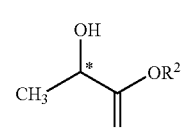

wherein $R^2$ represents a methyl group, ethyl group or isopropyl group, and * represents an asymmetric carbon, with trifluoromethanesulfonyl fluoride ($CF_3SO_2F$) in the presence of triethylamine (($C_2H_5$)$_3$N).

3. A process for producing an optically active α-fluorocarboxylate derivative represented by the formula [6],

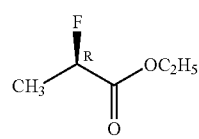

[6]

by reacting an optically active α-hydroxycarboxylate derivative represented by the formula [5],

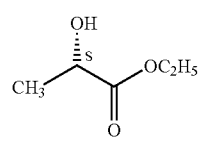

[5]

with trifluoromethanesulfonyl fluoride ($CF_3SO_2F$) in the presence of triethylamine (($C_2H_5$)$_3$N).

4. A production process according to claim 1, wherein only trifluoromethanesulfonyl fluoride ($CF_3SO_2F$) is used as a fluorination agent, and another fluorination agent is not used together.

5. A process for producing an optically active 2-fluoroalcohol derivative represented by the formula [7],

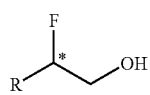

[7]

by reacting an optically active α-fluorocarboxylate derivative, which is represented by the formula [2],

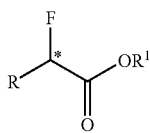

[2]

and which has been produced by the process according to claim 1, with a hydride reducing agent, in the formulas [2] and [7], R represents a straight-chain or branched-chain alkyl group of a carbon number of 1 to 12; one of or two by any combination of aromatic hydrocarbon groups, unsaturated hydrocarbon groups, straight-chain or branched alkoxy groups of a carbon number of 1 to 6, aryloxy groups, halogen atoms (fluorine, chlorine, bromine and iodine), protected carboxyl groups, protected amino groups or protected hydroxyl group can be substituted on any carbon atoms of the alkyl group; $R^1$ represents a straight-chain or branched-chain alkyl group of a carbon number of 1 to 8; any carbon atoms of the alkyl groups of R and $R^1$ may form a covalent bond; and * represents an asymmetric carbon.

6. A process for producing an optically active 2-fluoroalcohol derivative represented by the formula [8],

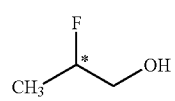

[8]

wherein * represents an asymmetric carbon, by reacting an optically active α-fluorocarboxylate derivative, which is represented by the formula [4],

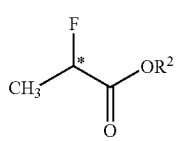

[4]

wherein $R^2$ is a methyl group, ethyl group or isopropyl group, and * represents an asymmetric carbon, and which has been produced by the process according to claim 2, with a hydride reducing agent.

7. A process for producing an optically active 2-fluoroalcohol derivative represented by the formula [9],

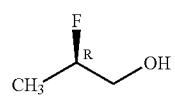

[9]

by reacting an optically active α-fluorocarboxylate derivative, which is represented by the formula [6],

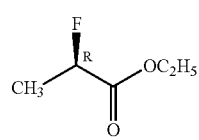

[6]

and which has been produced by the process according to claim 3, with a hydride reducing agent.

8. A production process according to claim 2, wherein only trifluoromethanesulfonyl fluoride ($CF_3SO_2F$) is used as a fluorination agent, and another fluorination agent is not used together.

9. A production process according to claim 3, wherein only trifluoromethanesulfonyl fluoride ($CF_3SO_2F$) is used as a fluorination agent, and another fluorination agent is not used together.

* * * * *